US006957581B2

(12) United States Patent
Gilgunn (10) Patent No.: US 6,957,581 B2
(45) Date of Patent: Oct. 25, 2005

(54) ACOUSTIC DETECTION OF MECHANICALLY INDUCED CIRCUIT DAMAGE

(75) Inventor: Peter Gilgunn, Pittsburgh, PA (US)

(73) Assignee: Infineon Technologies Richmond, LP, Sandston, VA (US)

( * ) Notice: Subject to any disclaimer, the term of this patent is extended or adjusted under 35 U.S.C. 154(b) by 169 days.

(21) Appl. No.: 10/695,394

(22) Filed: Oct. 29, 2003

(65) Prior Publication Data
US 2005/0092089 A1 May 5, 2005

(51) Int. Cl.[7] .................... G01N 29/24; G01N 29/26
(52) U.S. Cl. .............. 73/587; 438/5; 438/10; 438/14
(58) Field of Search .............. 73/579, 584, 587, 73/602; 438/5, 10, 14; 381/56

(56) References Cited

U.S. PATENT DOCUMENTS

| | | | |
|---|---|---|---|
| 4,655,673 A * | 4/1987 | Hawkes | 414/730 |
| 4,678,355 A * | 7/1987 | Gabor et al. | 400/389 |
| 6,052,243 A * | 4/2000 | Shimada | 360/46 |
| 6,105,432 A * | 8/2000 | Taniguchi et al. | 73/649 |
| 6,424,137 B1 | 7/2002 | Sampson | |
| 2002/0194915 A1 * | 12/2002 | Abdel-Malek et al. | 73/587 |
| 2003/0008597 A1 | 1/2003 | Tseng | |

* cited by examiner

Primary Examiner—Hezron Williams
Assistant Examiner—Rose M. Miller
(74) Attorney, Agent, or Firm—Staas & Halsey LLP (57) ABSTRACT

An apparatus and method thereof includes at least one acoustic transducer for receiving acoustic emissions produced during a semiconductor fabrication process. The acoustic transducer is mounted to various mechanical components of a semiconductor processing equipment in a manner so that the acoustic transducer receives acoustic emissions produced during the fabrication process. The received acoustic emissions are analyzed in in-situ to identify and determine surface characteristics of the wafer.

26 Claims, 8 Drawing Sheets

ACOUSTIC DETECTION OF MECHANICALLY INDUCED CIRCUIT DAMAGE

BACKGROUND OF THE INVENTION

1. Field of the Invention

The present invention relates to an acoustic detection apparatus and method to acoustically detect induced circuit damage caused by semiconductor manufacturing equipment handling systems.

2. Description of the Related Art

Fabricating an integrated circuit (IC) typically includes sequentially depositing conducting, semiconducting and/or insulating layers on a silicon wafer. One fabrication step includes depositing a metal layer over previous layers and planarizing the metal layer. For example, trenches or holes in an insulating layer may be filled with a conducting metal. After a chemical mechanical polishing (CMP) planarization, portions of the conductive metal remaining between the raised patterns of an insulating layer may form, for example, vias, plugs and/or lines.

Further, semiconductor processes take place under non-typical environmental conditions of temperature, pressure, atmospheric gaseous and liquid composition, and electromagnetic field intensity that are hostile to human life. Robots in a semiconductor manufacturing and handling equipment perform a movement of the silicon wafer, which is used as a raw material for integrated circuit (IC) pattern fabrication. If a robot ceases to operate or if a mechanical component of the semiconductor processing equipment is misaligned or malfunctioning, defects of the IC pattern on the silicon wafer may occur. Such defects may include scratching from the manufacturing or handling equipment coming into contact with the wafer or particles dispersed throughout the wafer from a manufacturing environment. However, current ex-situ control of defect monitoring processes employ visual inspection and/or optical testing of the silicon wafers to detect scratching. The ex-situ control inspects the silicon wafers after the manufacturing/handling processing of the silicon wafers is complete for an entire batch of wafers, that is, outside an environment where the manufacturing/handling processing occurs. Thus, if scratching occurs during first few manufacturing operations of the manufacturing of the IC pattern on the wafer, the wafer is not inspected for defects until after a number of manufacturing operations have occurred or after the manufacturing process is complete, which could be after many hours or days.

Due to batch processing considerations and other factors introducing delay between the manufacturing and analysis of the silicon wafers for scratching, a large number of the silicon wafers may become scratched by one of the mechanical components of the semiconductor processing equipment before such scratching is detected. For instance, during IC pattern manufacturing, a cassette holds about twenty-five wafers, with one centimeter between each wafer. Further, when the defective mechanical component is identified, production is stopped and corrective maintenance is performed on the equipment, thereby a significant time delay exists between occurrence of the scratching and detection of the defective mechanical component. Thus, typically a minimum of 25 wafers—and often as many as 400 wafers or more—may be damaged or destroyed before a detection of the problem.

Conventional systems typically use optical pattern recognition to determine defects on the IC pattern. In the optical pattern recognition, a known good circuit pattern is obtained prior to the manufacturing of the IC pattern. Then, the known circuit pattern is compared with the manufactured IC patterns to then determine whether both patterns are the same. If both patterns are different, the differences are identified to determine whether the differences are scratches or particles.

Accordingly, an apparatus and method are desired that detect in-situ a failure of mechanical components of the semiconductor manufacturing and handling equipment to significantly reduce an amount of scrapped production material.

SUMMARY OF THE INVENTION

According to an aspect of the present invention, there is provided a system to process a wafer, including: a semiconductor processing equipment including mechanical components to process the wafer; one or more acoustic transducers positioned on the mechanical components in a location of possible unwanted contact with the wafer and receiving acoustic emissions generated by the mechanical components and outputting signals indicative thereof; and a controller comparing in-situ the output signals with sound signals of each mechanical component to determine therefrom whether there is unwanted contact with the wafer, wherein the sound signals of each mechanical component correspond to the mechanical component not making unwanted contact with the wafer when processing the wafer.

According to an aspect of the present invention, there is provided a semiconductor processing method of a system including mechanical components to process a wafer, the method including: mounting one or more acoustic transducers on the mechanical components in a location of possible unwanted contact with the wafer; receiving acoustic emissions generated by the mechanical components and outputting signals indicative thereof; comparing in-situ the output signals with a sound signal to determine therefrom whether there is unwanted contact with the wafer, wherein the sound signals of each mechanical component correspond to the mechanical component not making unwanted contact with the wafer when processing the wafer According to an aspect of the present invention, there is provided a system initialization process for a normal production of an integrated circuit (IC) pattern of a wafer, including: acoustically auditing a semiconductor processing equipment to select mechanical components to be monitored; mounting one or more acoustic transducers and a recording device on the mechanical components selected for monitoring; monitoring each selected mechanical component only at predetermined manufacturing stages when there is a risk of the wafer from being damaged; recording output signals of the selected mechanical components when operating during the predetermined manufacturing stages; setting-up the mechanical components to make unwanted contact with a surface of the wafer; recording acoustic emission training set signals for pattern recognition of the output signals of the selected mechanical components when there is unwanted contact; adjusting back the selected mechanical components so that the mechanical components do not make unwanted contact with the surface of the wafer; recording the output signals generated by the selected mechanical components at the normal production as the sound signals; and beginning the normal production of the IC pattern and monitoring the output signals from the selected mechanical components for unwanted contact.

Various aspects and/or advantages of the invention will be set forth in part in the description that follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Reference will now be made in detail to the aspects of the present invention, examples of which are illustrated in the accompanying drawings, wherein like reference numerals refer to like elements throughout. The aspects are described below in order to explain the present invention by referring to the figures.

Figure 1A:
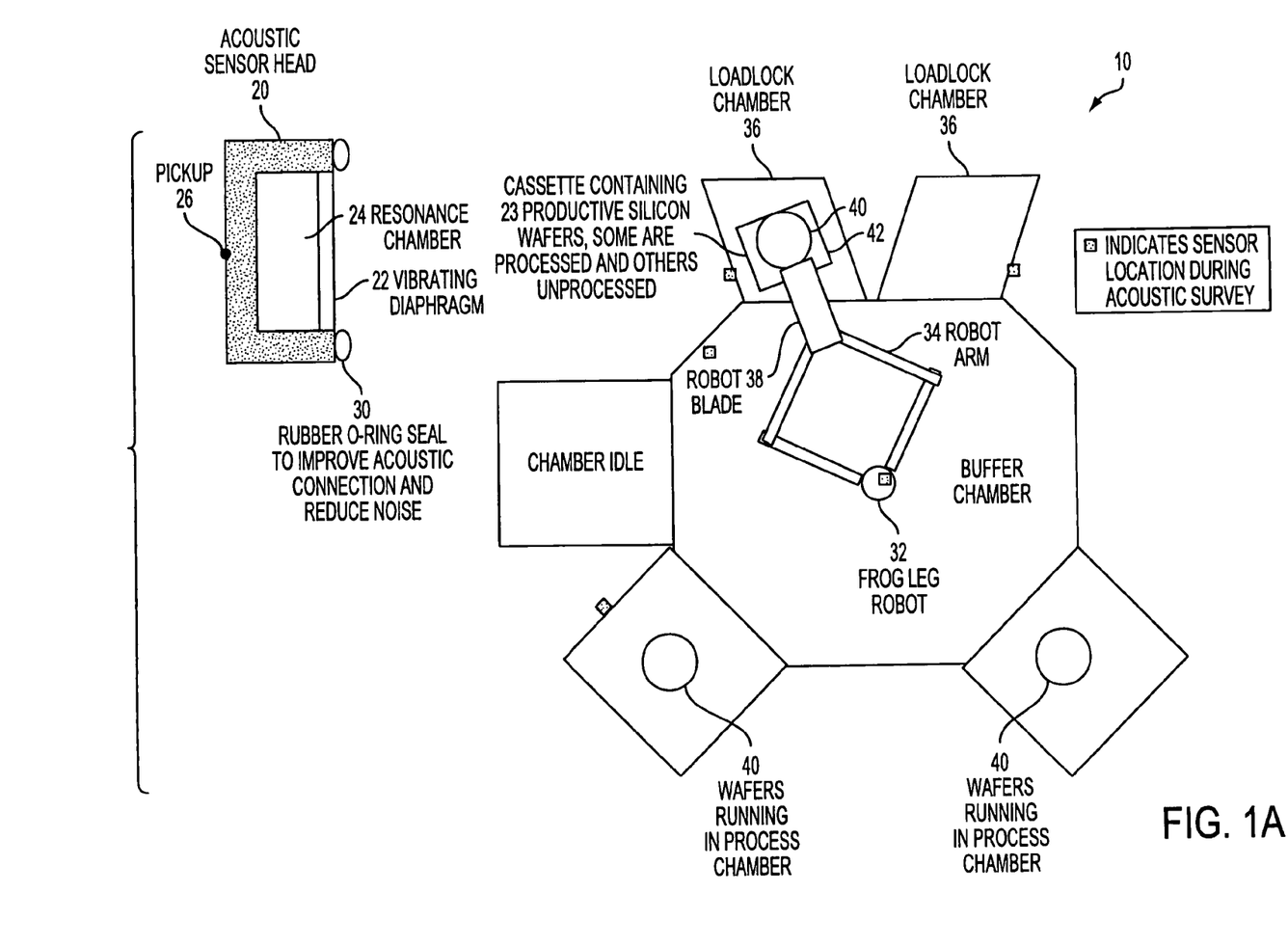
FIG. 1A is a diagram illustrating a system architecture using acoustic transducers 20, in accordance with an aspect of the present invention.

FIG. 1A is a diagram illustrating a system architecture using acoustic emission transducers 20 to detect an in-situ failure of mechanical components of a semiconductor processing equipment 10 to significantly reduce damage done to circuit patterns on semiconductor products and limit manufacturing costs and limit significant yield loss, in accordance with an aspect of the present invention. In-situ is defined as inspecting in real-time the semiconductor produce during the manufacturing/handling processing of the semiconductor product, that is, during a time where the manufacturing/handling processing of the semiconductor product occurs.

According to an aspect of the present invention, because different semiconductor processing equipment 10 or manufacturing tools have performing characteristics that are unique to that particular semiconductor processing equipment 10 or tool, an acoustic survey is performed on the semiconductor processing equipment 10 to determine which of the mechanical components of the semiconductor processing equipment 10 should include the acoustic transducer 20 to detect unwanted contact between the mechanical component of the semiconductor processing equipment 10 and a surface of a wafer 40 where an integrated circuit (IC) pattern is to be formed or to detect noise from unwanted dust particles that may be scratching the IC pattern. The present invention monitors the manufacturing/handling of the wafers 40 in-situ.

The semiconductor processing equipment 10 includes mechanical components that, at some point of the manufacturing or handling of the wafer 40, make contact with or are proximate to making contact with the wafer 40. Accordingly, during the manufacturing of the IC pattern and/or handling of the silicon wafer 40, when the mechanical components of the semiconductor processing equipment come into proximate contact with the wafer 40, the contact generates acoustic sound waves, which may be transmitted through the mechanical components and captured using the acoustic transducers 20 or sensors. The acoustic transducer 20, such as DEI 506T Audio Glass sensor or Sound Sensor (SS-OR) by Museum Tools Box, may be used in the present invention to capture the acoustic sound waves. Each mechanical component generates certain sounds, which are within a range of a predetermined normal sound signals and do not significantly affect a manufacturing quality of the IC pattern. The range may vary between different manufacturers of semiconductors. However, some sounds generated by each mechanical component may deviate outside the normal sound signals range, which would be representative of a significant amount of damage made to the wafer 40 by the mechanical component. For instance, a robot arm 34 of the semiconductor processing equipment moves in between two wafers 40 to pickup the wafer 40 to be processed, if the robot arm 34 drops or is off-set from a normal operating position, the robot arm 34 may scratch the wafer 40 that is underneath the wafer 40 that has been picked-up, thereby generating noises outside the range of the normal sound signals that the robot arm 34 may generate during a normal manufacturing/handling operation.

Figure 1B:
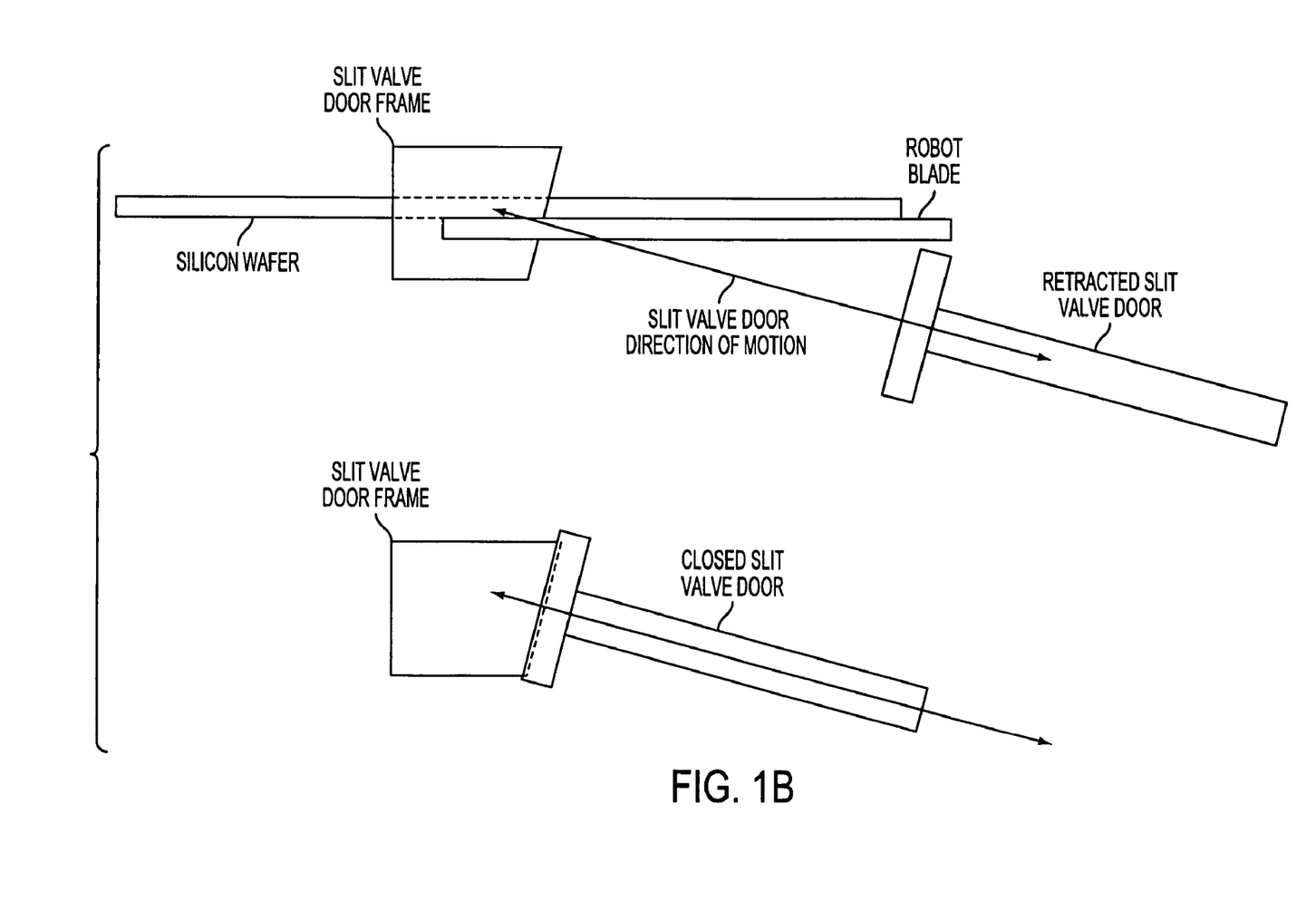
FIG. 1B is a diagram illustrating a slit valve door opening.

In accordance with an aspect of the present invention, some or all of the mechanical components making contact with the wafer 40 may be selected to include one or more acoustic transducers 20. For instance, the acoustic transducers 20 may be mounted on the robot arm 34 or a base of an axel on which the robot arm 34 rotates, on a base of a lead screw of a cassette stage 42 that holds the wafers 40 during processing, a buffer chamber, and/or on doorways or slit valve door openings between the buffer chamber and a process chamber of the semiconductor processing equipment 10, as shown in FIG. 1B. The acoustic transducer 20 includes a vibrating diaphragm 22 that senses the acoustic sound waves and transmits the acoustic sound waves as vibrations to a resonance chamber 24 within the acoustic transducer 20. A pickup unit 26 of the acoustic transducer 20 would then transmit output signals corresponding the vibrations to a controller 50, to be later described, which would analyze the output signals to determine therefrom whether corrective maintenance must be performed on the semiconductor processing equipment 10.

As shown in FIG. 1A, the semiconductor processing equipment 10 typically aligns and centers the wafers 40 and includes the robot arm 34 to load and unload the wafers 40 into a loadlock chamber 36 of the semiconductor processing equipment 10. A frog leg robot 32, the robot arm 34, and a robot blade 38 cooperate to load and unload the wafers 40 from the cassette stage 42. According to an exemplary aspect of the present invention, one or more acoustic transducers 20 may be situated on the frog leg robot 32 of the semiconductor processing equipment 10, on each loadlock chamber 36 housing the wafer cassette stage 42 including the wafers 40 during the manufacturing process, on each robot arm 34, and/or proximate to a contact region between the wafer 40 and the robot blade 38. In an alternative aspect of the present invention, the acoustic transducers 20 may be an integral part of the semiconductor processing equipment 10.

Figure 2:
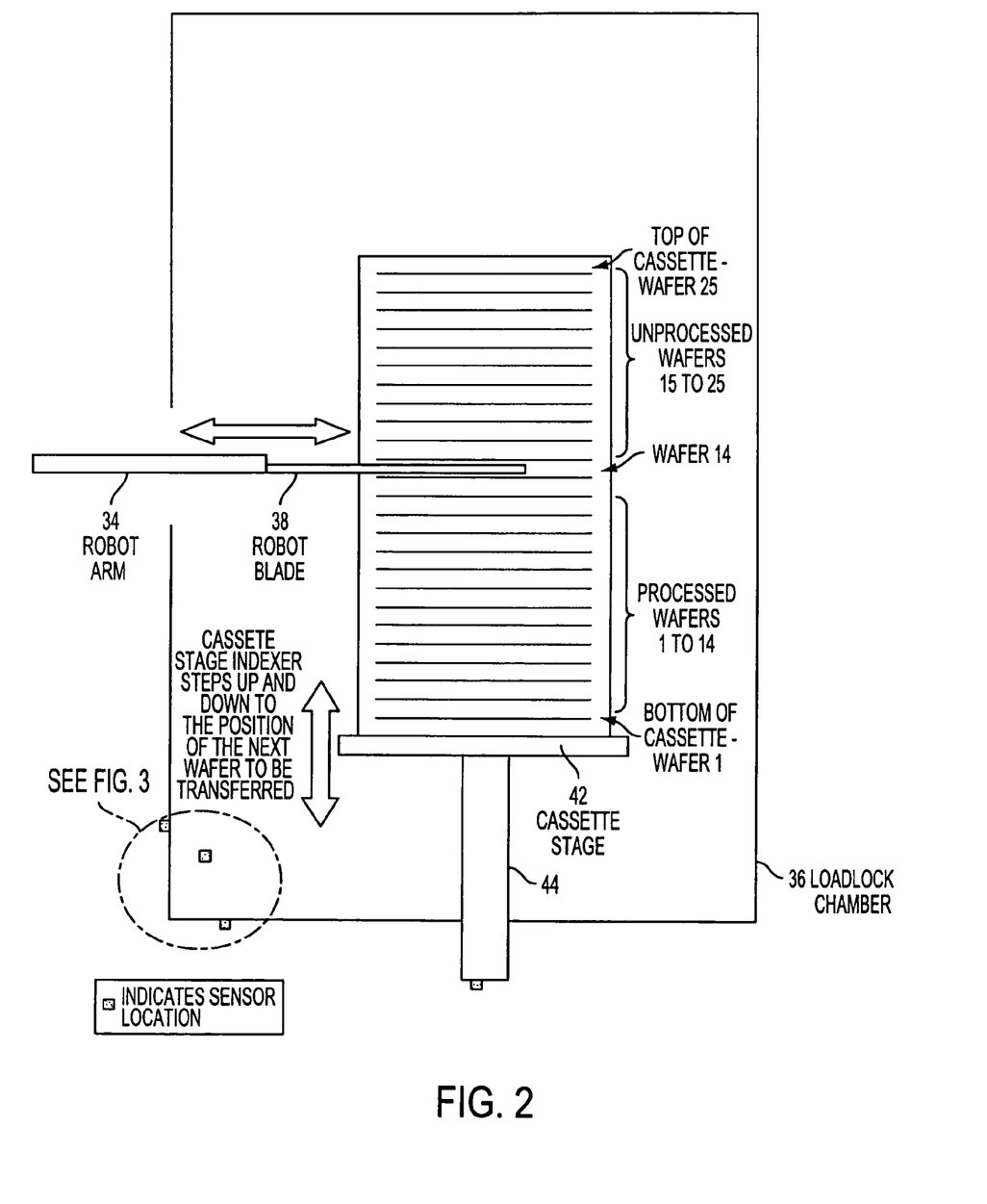
FIG. 2 is a diagram illustrating the acoustic transducers 20 on a loadlock housing a cassette stage including silicon wafers.
Figure 3:
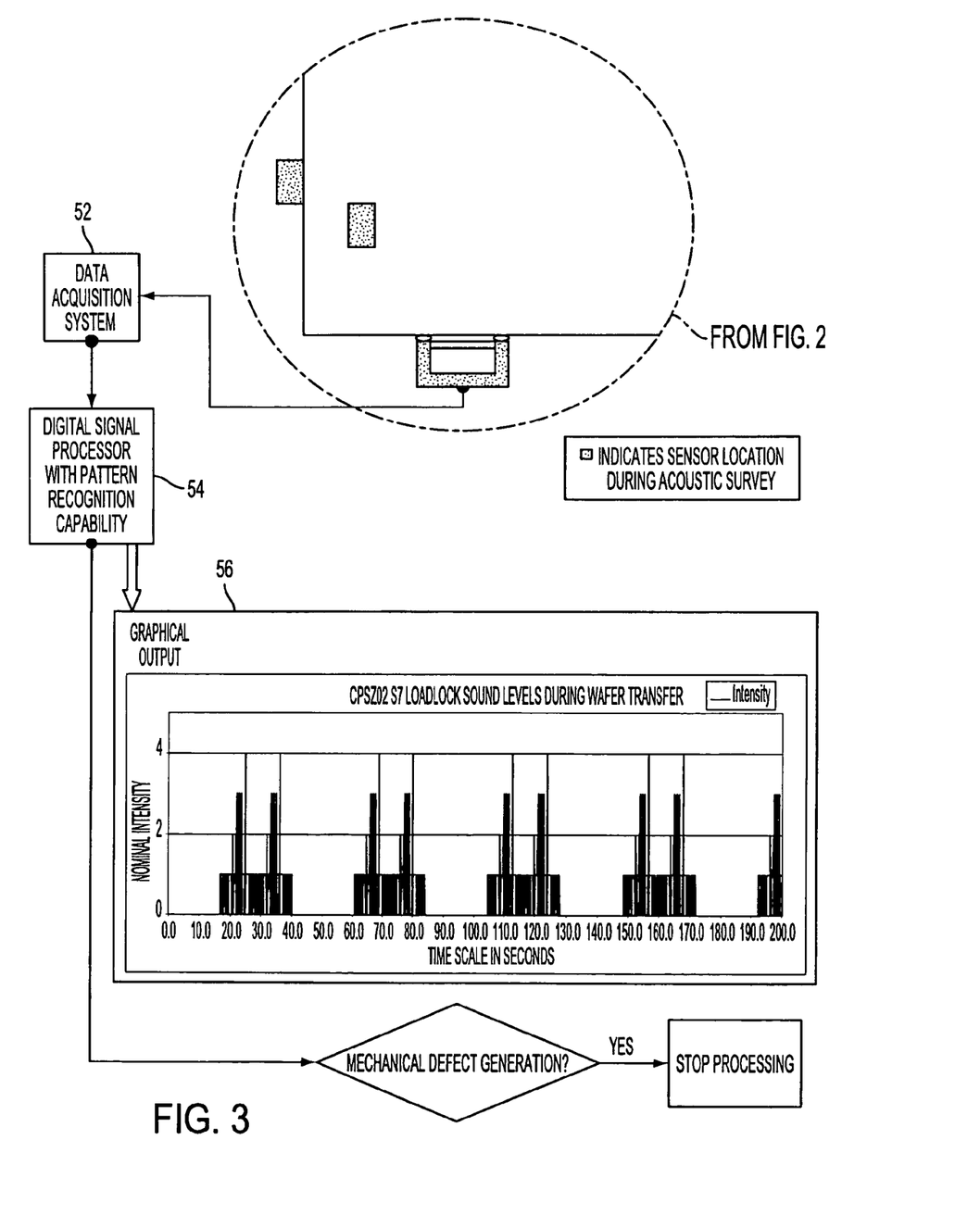
FIG. 3 is a diagram illustrating a screen of a semiconductor processing equipment displaying a number of defective silicon wafers detected in-situ, in accordance with an aspect of the present invention.

FIGS. 2 and 3 illustrate the acoustic transducers 20 mounted on various locations of the loadlock chamber 34 of the semiconductor processing equipment 10. One acoustic transducer 20 may be mounted on a base, on a sidewall, and/or an interior portion of the loadlock chamber 34. Also, another acoustic transducer 20 may be located on a driving mechanism 44 of the cassette stage 42 holding the wafers 40. As shown in FIG. 2, the robot blade 38 moves in and out of the cassette stage 42 through a slit valve picking up unprocessed wafers 40 and returning processed wafers 40. In an exemplary aspect of the present invention, during the IC pattern manufacturing on each wafer 40, a processed wafer 14 among twenty-five wafers, for instance, may risk IC pattern damage as the robot blade 38 moves over the processed wafer 14 to pick up unprocessed wafer 15. However, according to an aspect of the present invention, using acoustic emissions captured by the acoustic transducers 20, it is possible to determine whether the robot blade 38 is damaging the IC pattern is being damaged and whether the semiconductor processing equipment 10 should be stopped.

Figure 4:
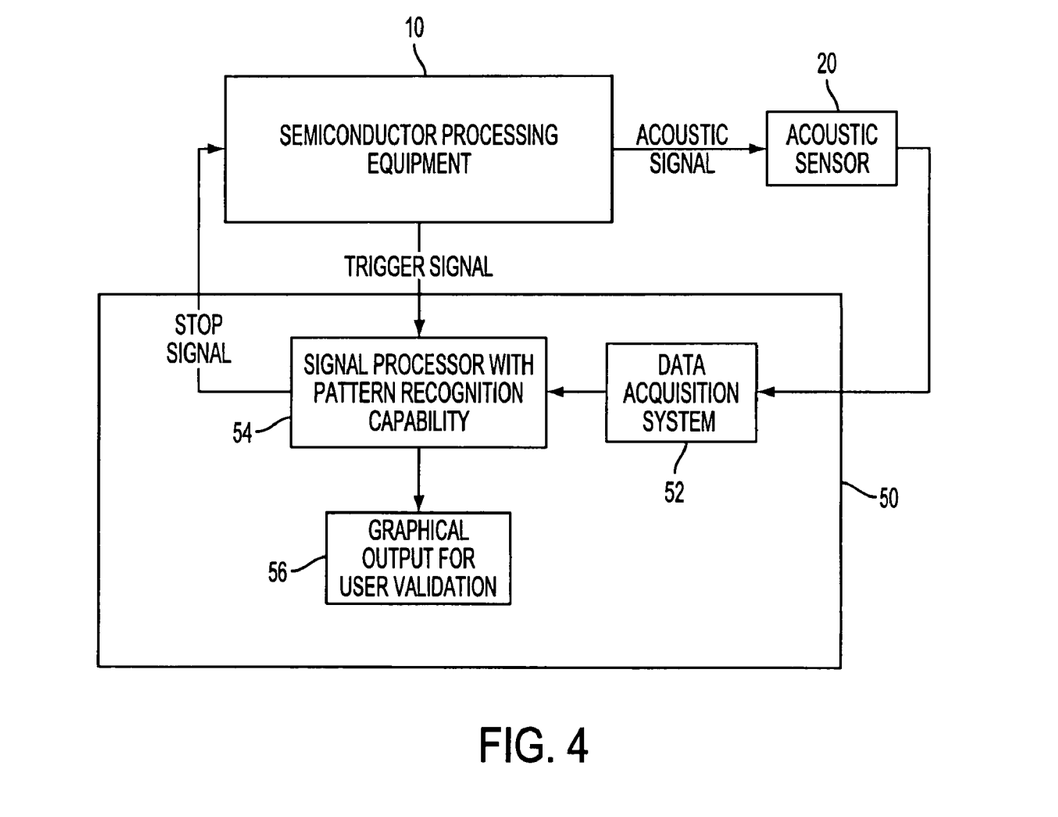
FIG. 4 illustrates a schematic diagram of the semiconductor processing equipment operatively connected to a controller, in accordance with an aspect of the present invention.

FIG. 4 illustrates a schematic diagram of the semiconductor processing equipment 10 operatively connected to the controller 50 and receiving output signals from the acoustic transducers 20 mounted on the semiconductor processing equipment 10. The acoustic transducer 20 for each mechanical component would receive the acoustic emissions and generate therefrom the output signals to the controller 50. The controller 50 receives the output signals from each acoustic transducer 20. The controller 50 also receives a trigger signal from each mechanical component associated with an acoustic transducer 20 triggering a digital signal processor 54 with pattern recognition capability to analyze the output signals corresponding to each acoustic transducer 20. Each output signal is indicative of measured acoustic waveforms associated with each mechanical component and the corresponding acoustic transducer 20 outputting the trigger signal.

Figure 5:
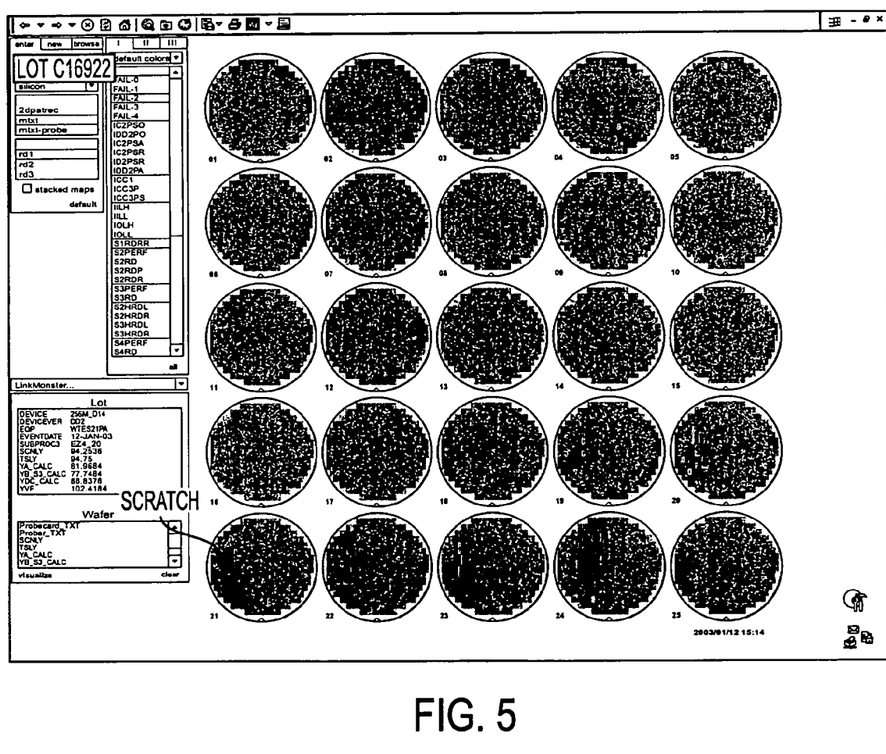
FIG. 5 is a diagram illustrating a graphical output displaying each silicon wafer to visually determine the wafers including scratches, according to an aspect of the present invention.

As shown in FIGS. 3 and 4, a data acquisition system 52 receives and stores the output signals and transfers the output signals to the signal processor 54. The signal processor 54 analyzes the output signals by comparing the output signals with the corresponding predetermined normal sound signals that correspond to a particular mechanical component of the semiconductor processing equipment 10. The signal processor 54 outputs a graphical output of the acoustic signals and the predetermined normal sound signals indicative of whether a significant amount of deviation exists between the acoustic signals and the predetermined normal sound signals. As shown in FIG. 3, if there is a significant amount of deviation, the controller 50 may automatically stop the processing of the silicon wafer 40 through a stop signal and output an alarm signal indicative thereof or may require an operator to manually stop the operation of the semiconductor processing equipment 10. A graphical output 56, such as a digital video screen, may graphically display the compared signals for the operator to validate or monitor. In an alternative aspect of the present invention, as illustrated in FIG. 5, the graphical output 56 may display each silicon wafer 40 allowing the operator to visually determine the wafers including scratches.

Figure 6:
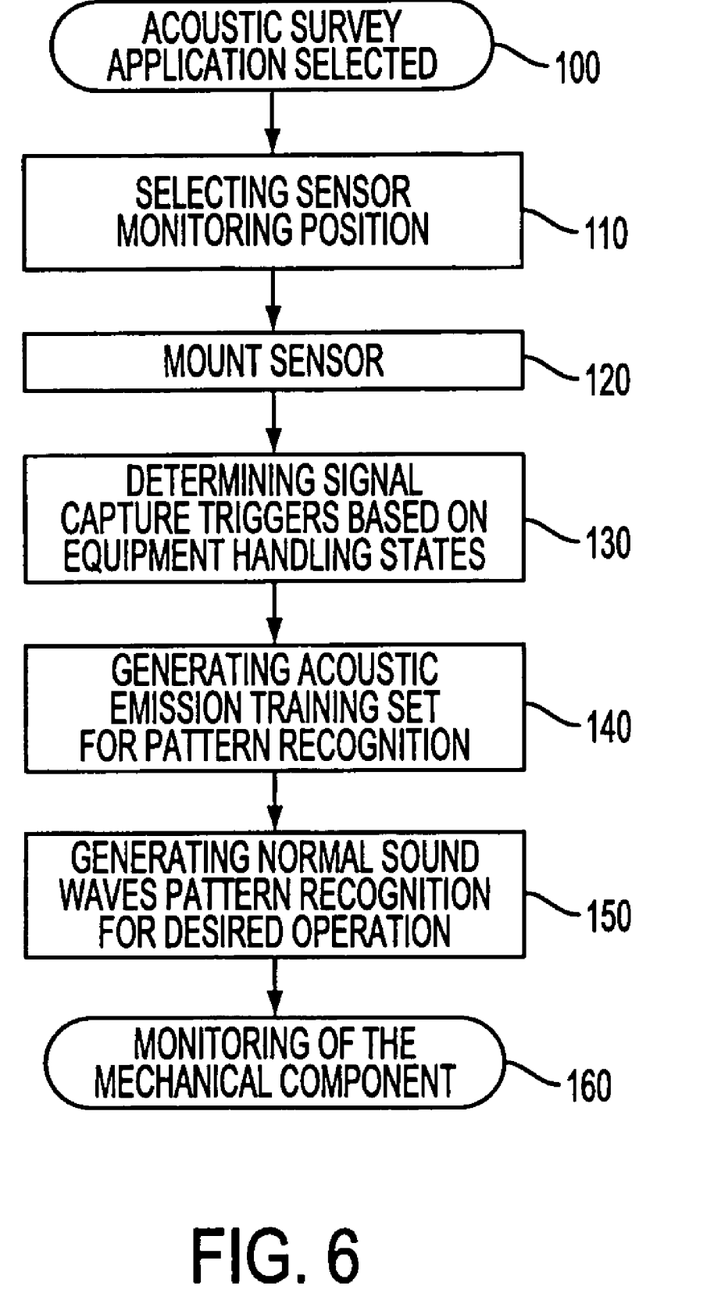
FIG. 6 illustrates a system initialization method, in accordance with an aspect of the present invention.

FIG. 6 illustrates a system initialization process, in accordance with an aspect of the present invention. Prior to obtaining the acoustic signals from a particular mechanical component and processing the output signals from the corresponding acoustic transducer 20, it is necessary to perform an acoustic survey to select which mechanical component of the semiconductor processing equipment 10 should be monitored and the normal sound signals that each selected mechanical component generates during a normal operation and during which no significant damage or scratching is done to the wafer 40 during processing. At operation 100, the acoustic survey application for the semiconductor processing equipment 10 to be monitored is selected. At operation 110, the semiconductor processing equipment 10 is acoustically audited to select the mechanical components to be monitored and to include the acoustic transducers 20. Usually, the mechanical components that are selected for analysis may be those components to be in contact with the surface of the wafer. Any type of recording device that is able to collect a wide range of frequencies may be used to read the acoustic emission picked-up by the acoustic transducers 20 from the mechanical components, such as an MP3 or a personal computer. At operation 120, at least one acoustic transducer 20 and the recording device are mounted on the mechanical component selected for monitoring.

At operation 130, in order to prevent an excess number of output signals being captured during the process, each mechanical component only needs to be monitored at predetermined manufacturing stages during the normal operation; in particular, when there is a risk of the IC pattern being damaged. For instance, when the mechanical component is not in operation, such as a stand-by manufacturing stage, it is not necessary to monitor the output signals from the acoustic transducer 20 mounted therein. It is not necessary, for instance, to obtain the output signals from the acoustic transducer 20 at the manufacturing stage when the robot arm 34 is not yet extended, as there is no risk of the IC pattern of being damaged. However, once the robot arm 34 extends, at that manufacturing stage, the process would be triggered to record the output signals. Thus, based on the selected manufacturing stages, the process begins recording the output signals of the mechanical component including the acoustic transducer 20 when the mechanical component operates during the selected manufacturing stages. The recording selected manufacturing stages of may be performed manually by the operator or in an autonomous manner, without any human intervention. In accordance with an aspect of the present invention, using a current flowing in an armature of the mechanical component may trigger the recording of the output signals. Also, the process may attach an event identification to the predetermined manufacturing stages that have been determined to be essential for the output signals to be recorded to provide an effective monitoring of the semiconductor processing equipment 10. Each output signal may be stored in the controller 50 with the corresponding event identification.

At operation 140, the mechanical component is set-up so that it scratches the surface of the wafer. Then, acoustic emission training set signals are recorded for pattern recognition of the output signals of the mechanical component when scratching. At operation 150, the mechanical component is adjusted back to the normal operation so that the mechanical component does not scratch the surface of the wafer and, while operating; the output signals generated by the mechanical component are recorded as the normal sound signals. At operation 160, normal production of the IC pattern begins and the output signals from the mechanical component are monitored during production. Operations 100 to 160 are repeated for each mechanical component that includes the acoustic transducer 20.

Figure 7:
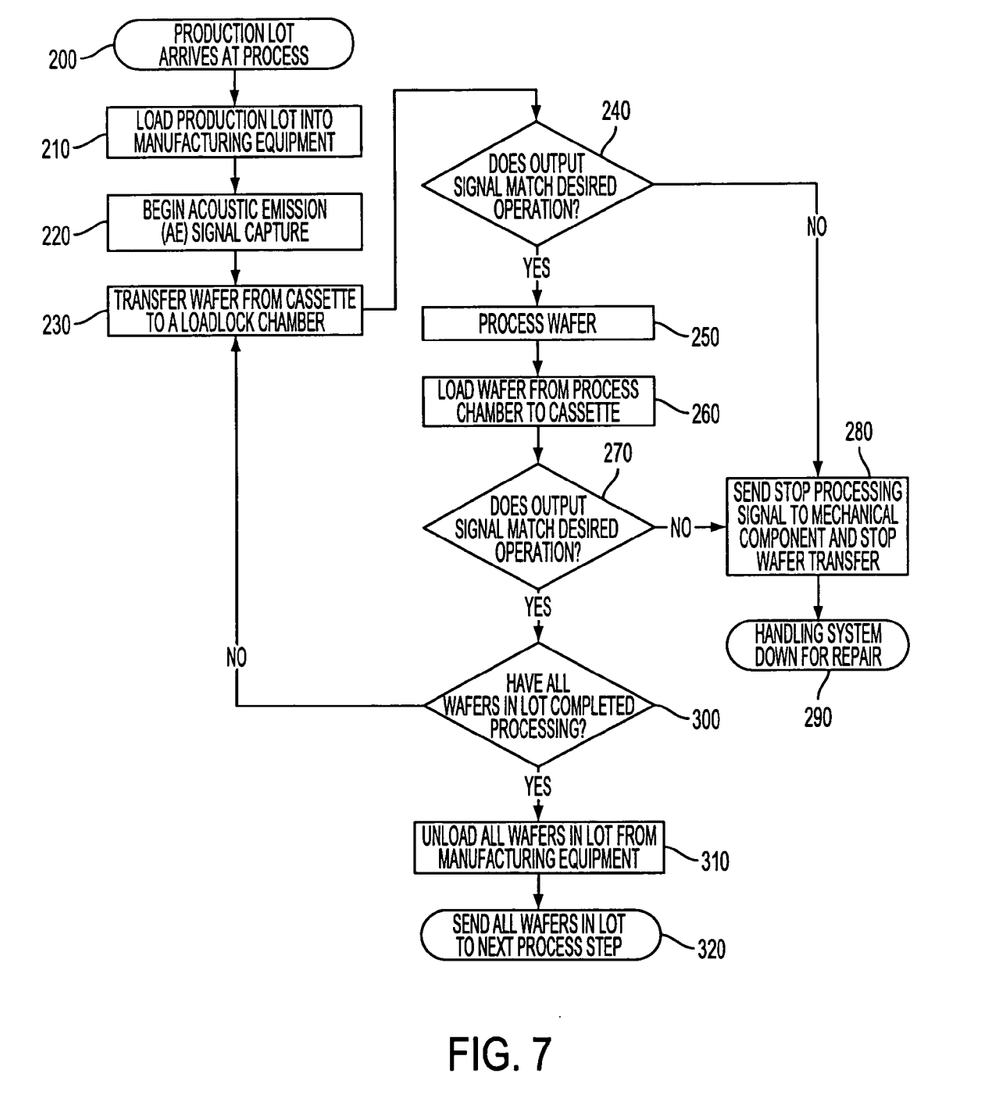
FIG. 7 illustrates a monitoring production method during a production operation, in accordance with an aspect of the present invention.

FIG. 7 illustrates a monitoring production method during a production operation, in accordance with an aspect of the present invention. The monitoring production method monitors and determines whether the output signal from each acoustic transducer 20 matches the corresponding normal sound signal. The monitoring production method may only monitor a particular mechanical component at the predetermined manufacturing stages when there is a risk that the particular mechanical component may damage the IC pattern. For illustrative purposes, the monitoring production method will be explained with respect to the monitoring of the robot arm 34 loading and unloading the wafer from the cassette stage 42. However, an ordinary person skilled in the art will appreciate that the same method may be applied to other mechanical components including the acoustic transducers 20.

At operation 200, the wafers or production lot is prepared for the manufacturing of the IC pattern. At operation 210, the wafers are loaded into the semiconductor processing equipment 10. At operation 220, the method begins to selectively monitor the acoustic emission signals using the acoustic transducers 20 and to selectively monitor and/or record the output signals from the acoustic transducers 20 at the selected manufacturing stages. At operation 230, one of the wafers 40 is transferred from the cassette stage 42 to the loadlock chamber 34. At operation 240, a determination is made as to whether the output signals from the acoustic transducer 20 of the robot arm 34 match the corresponding normal sound signals. If the output signals match the normal sound signals, which are indicative of the normal operation, then the method proceeds to operation 250. At operation 250, the wafer is processed to form the IC pattern. At operation 260, the wafer 40 on the loadlock chamber 34 is transferred back to the cassette stage 42. At operation 270, another determination is made as to whether the output signal matches the normal sound signal. If the output signals match the normal sound signals, which are indicative of the normal operation, then the method proceeds to operation 300. At operation 300, the method determines whether all the wafers 40 in the cassette stage 42 or in the lot have been processed. If all the wafers have been processed, at operation 310, all the wafers 40 in the cassette stage 42 or in the lot are unloaded from the semiconductor processing equipment 10 and, at operation 320, the wafers 40 are sent out for further processing.

However, if all wafers in the cassette stage 42 or in the lot have not been processed, then the method returns to operation 230. Also, if at operation 240 or at operation 270, it is determined that the output signals from the acoustic transducer 20 of the robot arm 34 do not match the corresponding normal sound signals then the method proceeds to operation 280. At operation 280, the method outputs a stop-processing signal to the robot arm 34 and the wafer transfer (i.e., loading or unloading) stops. The timing of the determination of whether the output signal matches the normal sound signal of a particular acoustic transducer 20 (i.e., operations 240 and 270) may vary depending on the manufacturing stages that were predetermined as being a stage where there is a risk that the particular mechanical component may damage the IC pattern.

According to an aspect of the present invention, a semiconductor processing equipment and method thereof includes at least one acoustic transducer for receiving acoustic emissions produced during a semiconductor fabrication process. The acoustic transducer is mounted to various mechanical components of the semiconductor processing equipment in a manner so that the acoustic transducer receives acoustic emissions produced during the fabrication process. The received acoustic emissions are analyzed in in-situ to identify and determine surface characteristics of the wafer.

The many features and advantages of the invention are apparent from the detailed specification and, thus, it is intended by the appended claims to cover all such features and advantages of the invention, which fall within the true spirit, and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A system to process a wafer, comprising:
    a semiconductor processing equipment comprising mechanical components to process the wafer;
    one or more acoustic transducers positioned on the mechanical components in a location of possible unwanted contact with the wafer and receiving acoustic emissions generated by the mechanical components and outputting signals indicative thereof; and
    a controller comparing in-situ the output signals with sound signals of each mechanical component to determine therefrom whether there is unwanted contact with the wafer, wherein the sound signals of each mechanical component correspond to the mechanical component not making unwanted contact with the wafer when processing the wafer.

2. The system as recited in claims 1, wherein the controller automatically stops the processing of the wafer when determining that there is unwanted contact with the wafer.

3. The system as recited in claims 1, wherein the controller performs an acoustic survey on the semiconductor processing system to determine which of the mechanical components to mount the acoustic transducers to detect the unwanted contact between the mechanical component and the wafer or to detect noise from unwanted dust particles that scratch the IC pattern.

4. The system as recited in claim 1, wherein when the output signals are outside a range of the sound signal, the controller automatically stops the processing of the wafer.

5. The system as recited in claim 1, wherein the semiconductor processing equipment further comprises:
    a cassette stage holding the wafer during processing;
    a buffer chamber; and
    a process chamber, wherein the acoustic transducers are mounted on the robot arm or a base of an axel on which the robot arm rotates, on a base of a lead screw of the cassette stage, the buffer chamber, and/or on doorways or slit valve door openings between the buffer chamber and the process chamber of the semiconductor processing equipment.

6. The system as recited in claim 5, wherein the semiconductor processing equipment further comprises:
    a frog leg robot; and
    a loadlock chamber housing the cassette stage, wherein the acoustic transducers are mounted on the frog leg robot, on the loadlock chamber, on the robot arm, proximate to a contact region between the wafer and a robot blade, on a driving mechanism of the cassette stage holding the wafer, and/or on a base, on a sidewall, and/or an interior portion of the loadlock chamber.

7. The system as recited in claim 1, wherein the acoustic transducers are an integral part of the semiconductor processing equipment.

8. The system as recited in claim 1, wherein when the controller receives the output signals from the acoustic transducers, the controller receives a trigger signal from each mechanical component triggering a pattern recognition to analyze the output signals corresponding to the acoustic transducers.

9. The system as recited in claim 1, wherein each output signal is indicative of measured acoustic waveforms associated with each mechanical component and the acoustic transducers outputting the trigger signal.

10. The system as recited in claim 1, wherein the controller further comprises:
   a signal processor having a pattern recognition capability to analyze the output signals of the acoustic transducers;
   a data acquisition system receiving and storing the output signals and transferring the output signals to the signal processor, wherein the signal processor analyzes the output signals by comparing the output signals with the corresponding sound signals, associated with the mechanical component.

11. The system as recited in claim 1, wherein the signal processor outputs a graphical output of the acoustic signals and the sound signals indicative of whether a significant amount of deviation exists between the acoustic signals and the sound signals.

12. The system as recited in claim 1, wherein when the controller automatically stops the processing of the wafer, the controller outputs an alarm signal indicative thereof.

13. The system as recited in claim 1, further comprising:
   a graphical output graphically displaying the compared signals or the wafer for an operator to validate or monitor.

14. The system as recited in claim 1, wherein the controller compares the output signals and the sound signals only at predetermined manufacturing stages when there is a risk of the wafer from being damaged.

15. A semiconductor processing method of a system comprising mechanical components to process a wafer, the method comprising:
   mounting one or more acoustic transducers on the mechanical components in a location of possible unwanted contact with the wafer;
   receiving acoustic emissions generated by the mechanical components and outputting signals indicative thereof;
   comparing in-situ the output signals with a sound signal to determine therefrom whether there is unwanted contact with the wafer, wherein the sound signals of each mechanical component correspond to the mechanical component not making unwanted contact with the wafer when processing the wafer.

16. The method as recited in claims 15, further comprising:
   automatically stopping the processing of the wafer when determining that there is unwanted contact with the wafer.

17. The method as recited in claim 15, further comprising:
   performing an acoustic survey to select the mechanical components to be monitored and the sound signals that each selected mechanical component generates during a normal operation and during which no significant damage or scratching is done to the wafer during processing.

18. The method as recited in claim 15, further comprising:
   when receiving the output signals from the acoustic transducers, receiving a trigger signal from each mechanical component triggering a pattern recognition to analyze the output signals corresponding to the acoustic transducers.

19. The method as recited in claim 15, wherein the signal processor outputs a graphical output of the acoustic signals and the sound signals indicative of whether a significant amount of deviation exists between the acoustic signals and the sound signals.

20. The method as recited in claim 15, wherein the processing of the wafer is automatically stopped and further comprising:
   outputting an alarm signal indicative that the processing of the wafer is automatically stopped.

21. The method as recited in claim 15, further comprising:
   graphically displaying the compared signals or the wafer for an operator to validate or monitor.

22. The method as recited in claim 15, wherein the comparing of the output signals and the sound signals is performed only at predetermined manufacturing stages when there is a risk of the wafer from being damaged.

23. A system initialization process for a normal production of an integrated circuit (IC) pattern of a wafer, comprising:
   acoustically auditing a semiconductor processing equipment to select mechanical components to be monitored;
   mounting one or more acoustic transducers and a recording device on the mechanical components selected for monitoring;
   monitoring each selected mechanical component only at predetermined manufacturing stages when there is a risk of the wafer from being damaged;
   recording output signals of the selected mechanical components when operating during the predetermined manufacturing stages;
   setting-up the mechanical components to make unwanted contact with a surface of the wafer;
   recording acoustic emission training set signals for pattern recognition of the output signals of the selected mechanical components when there is unwanted contact;
   adjusting back the selected mechanical components so that the mechanical components do not make unwanted contact with the surface of the wafer;
   recording the output signals generated by the selected mechanical components at the normal production as the sound signals; and
   beginning the normal production of the IC pattern and monitoring the output signals from the selected mechanical components for unwanted contact.

24. The process as recited in claim 23, wherein the recording selected manufacturing stages of is performed manually by the operator or in an autonomous manner, without any human intervention.

25. The process as recited in claim 23, wherein a current flowing in an armature of the mechanical components triggers the recording of the output signals.

26. The process as recited in claim 23, further comprising:
   attaching an event identification to the predetermined manufacturing stages.

* * * * *

UNITED STATES PATENT AND TRADEMARK OFFICE
CERTIFICATE OF CORRECTION

PATENT NO. : 6,957,581 B2  Page 1 of 1
APPLICATION NO. : 10/695394
DATED : October 25, 2005
INVENTOR(S) : Gilgunn It is certified that error appears in the above-identified patent and that said Letters Patent is hereby corrected as shown below:

Column 8, line 33, change "claims 1," to --claim 1,--

Column 8, line 36, change "claims 1," to --claim 1,--

Column 9, line 54, change "claims 15," to --claim 15,--

Column 10, line 54, change "of is" to --is--

Signed and Sealed this

Fifteenth Day of August, 2006

JON W. DUDAS
*Director of the United States Patent and Trademark Office*